United States Patent [19]

Stitt et al.

[11] Patent Number: 5,567,598

[45] Date of Patent: Oct. 22, 1996

[54] MICROBIAL MONITORING DEVICE

[75] Inventors: David T. Stitt, Freeland, Md.; Gregory J. Burrell, Red Lion, Pa.; Kwok-Yu Hu, Eilicott City, Md.; James F. Monthony, Baltimore, Md.; Robert Sapitowicz, Abingdon, Md.

[73] Assignee: Becton Dickinson and Company, Franklin Lakes, N.J.

[21] Appl. No.: 25,899

[22] Filed: Mar. 3, 1993

Related U.S. Application Data

[63] Continuation of Ser. No. 687,359, Apr. 18, 1991, abandoned.

[51] Int. Cl.$^6$ .................................................. C12Q 1/18
[52] U.S. Cl. ........................... 435/29; 435/7.32; 435/32; 435/39; 435/968; 436/172; 436/800
[58] Field of Search ...................... 436/800, 172; 435/29, 33, 32, 301, 968, 39, 7.32, 288.4

[56] References Cited

U.S. PATENT DOCUMENTS

| | | | |
|---|---|---|---|
| 3,509,026 | 4/1970 | Sauders | 435/33 |
| 3,612,866 | 10/1971 | Stevens . | |
| 4,643,968 | 2/1987 | Weaver | 435/32 |
| 4,798,788 | 1/1989 | Sands . | |
| 4,810,655 | 3/1989 | Khalil et al. . | |
| 4,824,789 | 4/1989 | Yafuso et al. . | |
| 5,030,420 | 7/1991 | Bacon et al. | 422/82.07 |

FOREIGN PATENT DOCUMENTS

| | | | |
|---|---|---|---|
| 0333253 | 9/1989 | European Pat. Off. | C12M 1/34 |
| 0448923 | 10/1991 | European Pat. Off. | C12Q 1/04 |
| 3346810 | 7/1984 | Germany | G01N 21/62 |
| 2132348 | 7/1984 | United Kingdom . | |

OTHER PUBLICATIONS

M. T. Pezzlo et al., Rapid Bioluminescence Method for Bacteriuria Screening, 1989, Journal of Clinical Microbiology, pp. 716–720.

E. R. Carraway et al., Luminescence Quenching Mechanism for microheterogeneous Systems, 1991, Anal. ChemI., pp. 332–336.

E. R. Carraway et al., Photophysics and Photochemistry of Oxygen Sensors Based on Luminescent Transition–Metal Complexes, 1991, Anal. Chem., pp. 337–342.

A. Sharma et al., Fiberoptic Oxygen Sensor Based on Fluorescene Quenching and Energy Transfer, 1988, Applied Spectroscopy, vol. 42, No. 6, pp. 1009–1011.

A. Sharma et al., Unusually Efficient Quenching of the Fluorescence of an Energy Transfer–Based Optical Sensor for Oxygen, 1988, Analytica Chimica Acta, 212, pp. 261–265.

E. D. Lee et al., Luminescence Ratio Indicators for Oxygen, 1987, Anal. Chem., pp. 279–283.

J. R. Bacon et al., Determination of Oxygen Concentrations by Luminescence Quenching of a Polymer–Immobilized Transition–Metal Complex, Anal. Chem., vol. 59, No. 23, pp. 2780–2785, (1987).

L. B. McGown et al., A New Fluorimetric Method for Measurement of Oxidase–Catalyzed Reactions, 1980, Analytica Chimica Acta, 117, pp. 363–365.

M. E. Cox and B. Dunn, Detection of oxygen by fluorescence quenching Jul. 15, 1985, Applied Optics, vol. 24, No. 14, pp. 2114–2120.

Noffsinger, et al. Anal Chem. 59:865–868 1987.

Hoal, et al. Anal Chem. 60:834–837.

*Primary Examiner*—Esther M. Kepplinger
*Assistant Examiner*—Milton I. Cano
*Attorney, Agent, or Firm*—Susan A. Capello

[57] ABSTRACT

This invention presents methods for detection and evaluation of metabolic activity of microorganisms based upon their ability to consume dissolved oxygen. The methods utilize a fluorescence detection system which makes use of the sensitivity of the fluorescent emission of certain compounds to the presence of oxygen, which quenches (diminishes) the compound's fluorescent emission in a concentration dependent manner. Respiring microorganisms will affect the oxygen concentration of a liquid medium in which they are immersed. Thus, this invention provides a convenient system to gather information on the presence, identification and metabolic activity of microorganisms by determining their effect on the oxygen concentration of the media in which they are present.

34 Claims, 7 Drawing Sheets

MICROBIAL MONITORING DEVICE

This is a continuation of application Ser. No. 07/687,359 filed on Apr. 18, 1991 now abandoned.

BACKGROUND OF THE INVENTION

Our environment contains a multitude of microorganisms with which we are continuously interacting. These interactions can be beneficial, e.g. fermentations to produce wine, vinegar or antibiotics; neutral; or even harmful, as in the case of infectious diseases. The ubiquitous presence of these microorganisms, thus, creates a continuing need for the detection, identification and study of the presence and metabolic activity of such microorganisms.

While the science of microbiology has changed significantly in the last 25 years, many procedures for the detection, identification and analysis of the behavior of microorganisms are still time consuming. For example, in the area of antimicrobic susceptibility testing nearly half of all testing in hospitals in the United States still use the Bauer-Kirby Disc Method. This method uses the presence or absence of visible growth of the microorganisms to indicate the efficacy of an antimicrobic compound, and generally requires an 18 to 24 hour incubation period to allow for microorganism growth before a result can be obtained. A decrease in the time required to obtain such antimicrobic susceptibility information is needed.

Another popular method for antimicrobic susceptibility testing is the broth micro-dilution method, such as the Sceptor® System for identification and antimicrobic susceptibility testing of organisms (Becton Dickinson Diagnostic Instrumentation Systems, Sparks, Md.). The system uses a disposable plastic panel having a plurality of low volume cupulas (ca. 0.4 ml per cupula), each containing a different test compound or a different concentration of a test compound dried on the cupula surface. The organism to be tested is suspended in the desired testing medium, and aliquots are delivered to the individual cupulas of the test panel. The reagent dried on the panel dissolves in the sample, and the system is then incubated overnight (18 to 24 hrs.) to allow sufficient time for the organisms to interact with the reagent and for visible growth to appear. The panel is subsequently examined visually for the presence or absence of growth, thereby obtaining information on the susceptibility of the organism undergoing testing. Additional wells aid in identifying the organism. However, this test method suffers from the drawback of also requiring a long incubation period.

One approach to the reduction of the incubation time is to monitor metabolic activity of the microorganisms, rather than growth of colonies. Many approaches have been reported in the attempt to rapidly and accurately monitor such metabolic activity.

For example, apparatus utilizing light scattering optical means have been used to determine susceptibility by probing the change in size or number of microorganisms in the presence of various antimicrobic compounds. Commercial instruments utilizing these principles are exemplified by the Vitec System (BioMerieux Corp.). This system claims to yield information on antimicrobic susceptibility of microorganisms within 6 hours for many organism and drug combinations. Other combinations can require as long as 18 hours before the antimicrobic susceptibility of the organism can be determined by this machine.

Additionally, modifications of the Bauer-Kirby procedure have been developed which allow certain samples to be read in four to six hours. However, such a system is "destructive" in nature, requiring the spraying of a developing solution of a color forming dye onto the test plate. Re-incubation and reading at a later time is, thus, not possible and if the rapid technique fails, the experiment cannot be continued for a standard evaluation at a later time.

A bioluminescent method based on the quantity of ATP present in multiplying organisms has been described as yielding results of antimicrobic susceptibility testing in four and half hours for certain compositions (Wheat et al.). However, the procedure tends to be cumbersome and broad applicability has not been shown.

Other approaches have involved monitoring of microbial oxygen consumption by the measurement of pH and/or hemoglobin color change, or by the use of dyes such as triphenyl- tetrazolium chloride and resazurin, that change color in response to the total redox potential of the liquid test medium.

The monitoring of the consumption of dissolved oxygen by microorganisms, as a marker of their metabolism, has been studied for many years. For example, C. E. Clifton monitored the oxygen consumption of microorganisms over a period of several days using a Warburg flask in 1937. This method measured the change in oxygen concentration in a slow and cumbersome manner.

The "Clark" electrode, a newer electrochemical device, is also commonly used to measure dissolved oxygen. Unfortunately, the Clark electrode consumes oxygen during use (thereby reducing the oxygen available to the microorganisms) and the "standard" size electrode is typically used only to measure volumes of 100 mls or greater to prevent the electrode from interfering with the measurements.

A "miniature" Clark electrode has been described, but this electrode is a complicated multi-component part which must, also, be in contact with the solution to be measured. While an oxygen permeable membrane can be used to prevent the electrode components of the device from interacting with the constituents of the test solution, the oxygen must still equilibrate between the test solution and the measurement system and is consumed once it passes the membrane.

Optical systems which can yield oxygen concentration data, have been developed to overcome the shortcomings of the Clark electrode systems. The main advantage of such optical methods is that the instrumentation required to determine quantitative value does not itself make physical contact with the test solution. Optical techniques allowing both colorimetric and fluorometric analyses for oxygen to be carried out rapidly and reproducibly are known, and costs for such analyses are often quite low. For example, several luminescent techniques for the determination of oxygen have been described which are based on the ability of oxygen to quench the fluorescence or phosphorescence emissions of a variety of compounds. However, such methods have not been adapted to microbial monitoring.

Other systems have been described that provide information on the presence, identity and antimicrobic susceptibility of microorganisms in a period of eight hours or less. Wilkins and Stones in U.S. Pat. No. 4,200,493 disclose a system that uses electrodes and a high impedance potentiometer to determine the presence of microorganisms. In U.S. Pat. No. 3,907,646 Wilkins et al disclose an analytical method which utilizes the pressure changes in the headspace over a flask associated with microbial growth for the detection and surveillance of the organisms. U.S. Pat. No. 4,220,715 to Ahnell, discloses a system wherein the head space gas above a test sample is passed through an external oxygen detector for determination of the presence of microorganisms. Ahnell, in U.S. Pat. No. 4,152,213, discloses a system for analysis by monitoring the vacuum produced by growing organisms in a closed head space above a test sample. U.S. Pat. No. 4,116,775 to Charles et. al is an example of the use of optical means based on the increase in turbidity or optical density of a growing microbial culture for the detection and monitoring of bacterial growth. A combined electro-optical measurement of birefringence of a test solution containing microorganisms is described in EPO 0092958 (Lowe and Meltzer).

It becomes apparent that a wide variety of methods have been applied to the detection and the antibiotic susceptibility testing of microorganisms. Many of these methods can only yield useful data when monitored by instruments dedicated to this task. Thus there exists a need for a system which can allow determinations of the presence and behavior of microorganisms without the requirement of dedicated instrumentation. Further there exists a need for a system that will allow the determination of the effect of a compound such as an antibiotic on a sample of microorganisms in a short time that does not significantly alter the behavior of the microorganisms.

SUMMARY OF THE INVENTION

It is therefore an object of this invention to provide an improved means to detect the presence of, and to evaluate the metabolic activity of, microorganisms present in a liquid or semi-solid media. It is further an object of this invention to provide a microbial monitoring device or system which can be simply read and visually interpreted, and which permits results to be obtained in a shorter time period than previously attainable, nominally 6 hours or less. Additionally, it is an object of the invention to provide a means for detection and/or monitoring the activity of oxygen consuming enzymes or enzyme systems without the use of dedicated instrumentation.

The above and related objects are realized by the processes of the instant invention. These processes use a fluorescence detection system wherein the fluorescing sensor compound is one which exhibits a quantifiable degree of quenching when exposed to oxygen. This sensor compound is brought into contact with the test sample (either directly or separated by an oxygen permeable membrane) and the fluorescence is measured or observed visually with appropriate aids. An increase in fluorescence is indicative of respiring aerobic microorganisms, which utilize (and thereby reduce) the oxygen in the sample.

The system can, thus, be used to detect a variety of respiring microorganisms. It is further anticipated that this system can be used to detect the presence of $O_2$ dependent compositions such as enzymes.

DETAILED DESCRIPTION OF INVENTION

The process of this invention presents a quick, easy, and unambiguous method for the measurement and/or detection of respiring aerobic microorganisms by measurement or visual observation of fluorescence. The fluorescent sensor compound is irradiated with light containing wavelengths which cause it to fluoresce, and the fluorescence is measured by any standard means, or evaluated visually.

The fluorescent compound must be one which exhibits a large quenching upon exposure to oxygen at concentration ordinarily found in the test liquids (generally 0.4%). While virtually any such compound can be used, preferred fluorescent compounds of this invention are tris-2,2'-bipyridyl ruthenium (II) salts, especially the chloride hexahydrate salt (Ru(BiPy)$_3$Cl$_2$), tris-4,7-diphenyl-1,10-phenanthroline ruthenium (II) salts, especially the chloride (salt Ru(DPP)$_3$Cl$_2$), and 9,10-diphenyl anthracene (DPA).

The fluorescent compound must be placed in chemical communication with the oxygen of the test sample to exhibit the quenching. This can be achieved by placing the compound directly in contact with the sample. However, in a preferred embodiment the compound and sample are separated from each other by the interposition of a membrane embedding material permeable to oxygen, and relatively impermeable to the other sample components, between them, thereby preventing the interaction of the sample and the compound.

The system can be allowed to interact unobserved for a predetermined amount of time after which the presence or absence of fluorescence is observed and compared to appropriate control samples, yielding results that are often obtained with a single such observation. A particular benefit of this system, is that the measurement of fluorescence is non-destructive and if after a period of time (e.g. 4 hours) the results are non-conclusive, the system can be re-incubated and read again at a later time. Further, while it is anticipated that the results will be compared with reagent controls, such is by no means necessary, and it is postulated that, by appropriate choice of fluorescent compounds, a skilled technician or technologist would be capable of independently determining whether the results indicate the presence of microbial activity.

The detection of fluorescent intensity can be performed by any means ordinarily used for such measurements, e.g. a fluorometer. Alternatively, the fluorescent intensity can be observed visually and, optionally, compared with a reagent control (e.g. a system containing no live organisms or a system with no added test chemicals). Thus, the methods can be utilized to both provide a quantitative measurement of relative activity, using a fluorometer, or a more qualitative estimate of such activity, by visual inspection.

In a preferred embodiment of this invention, the fluorescent compound is chosen such that it will exhibit little or no fluorescence in the presence of oxygen. This obviates the need for a control, as the person performing the test would interpret any appreciable fluorescence (i.e. beyond that of any nominal background fluorescence) as indicative of the presence of microbial activity. Such results can be obtained by a fluorometer or other measurement means, or preferably, visual inspection, and provide a quick, qualitative estimate of such activity. Preferred fluorescent compounds for this embodiment include $Ru(BiPy)_3Cl_2$ and $Ru(DPP)_3Cl_2$.

It has also been found that, while the test can be run in systems isolated from atmospheric oxygen, accurate results can also be obtained when the system is left exposed to atmospheric oxygen. In fact, this is desirable when the organisms are to be incubated for periods of time exceeding 2 hours, as they would otherwise tend to consume all the dissolved oxygen in the system and subsequently generate a false reading. Thus, the system of this invention is quite versatile, and can be used in a wide array of conditions.

A further benefit of the instant invention is that a unitized apparatus can be constructed. Briefly, the apparatus comprises a sample containing reservoir, or more commonly a plurality of identical reservoirs adapted to contain a test sample and other such liquid and soluble components (e.g. nutrients, etc.) as may be required by the particular application. The reservoirs also provide a fluorescent indicator element which monitors the oxygen levels of the solution. The indicator element of this invention uses a fluorescent compound known to show a large quenching of its fluorescent emission when exposed to oxygen.

In a preferred embodiment of this invention, the fluorescent compound can be mixed and distributed throughout a plastic or rubber phase that is permeable to oxygen gas but relatively impermeable to water and non-gaseous solutes. Silicone rubber is a particularly useful material for this application. When a test solution containing microorganisms is placed in such a sample reservoir, the metabolic activity of the organisms causes a reduction in the level of dissolved oxygen in the sample, and the sample will yield a higher fluorescent signal upon excitation. Sample liquids not containing microorganisms will not show a decrease in their oxygen levels and will only show low levels of fluorescence due to high oxygen quenching of fluorescence.

Alternatively, the oxygen sensitive fluorophore can be in a microencapsulated form or in the form of granules of an oxygen permeable material. It is also anticipated that the fluorophore can be contained within a separately manufactured component such as a bead, disc, or prongs which can be separately introduced into the test solution. The use of prongs is particularly advantageous as such prongs can be attached to a lid or other device to permit easy manipulation. In a preferred embodiment, a plurality of prongs can be attached to a single membrane, or other cover and thereby be maintained in an appropriate orientation such that they can simultaneously be placed into the reservoirs of a base containing a plurality of sample reservoirs. By choice of appropriate materials, the prongs can be made impermeable to the indicator molecules and to microorganisms in the sample, but permeable to oxygen.

The fluorophore can also be in a liquid phase separated from the solution being analyzed by a membrane that is impermeable to the indicator molecules and to microorganisms in the sample but which is permeable to oxygen. Additionally, less-sensitive sensors can be fabricated by using less $O_2$ permeable polymers or by using compounds with shorter excited-state lifetimes.

Further, the methods of this invention can be used to test the susceptibility of a microorganism to a compound, such as an antibiotic, which is capable of severely inhibiting the growth and/or the metabolic activity of organisms. The increase in fluorescent signal normally caused by the organism will be suppressed in the presence of such compounds. The behavior of the fluorescent signal from a reservoir will demonstrate the ability of the test component to negatively effect the normal oxygen consumption of the organism added to the reservoir.

EXAMPLES

The following examples illustrate certain preferred embodiments of the instant invention but are not intended to be illustrative of all embodiments.

EXAMPLE 1

Preparation of an $O_2$-Sensitive Indicator Microtitration Tray

The fluorescent compound tris 4,7-diphenyl-1,10phenanthroline ruthenium (II) chloride ($Ru(DPP)_3Cl_2$) was synthesized using the procedure of Watts and Crosby (J. Am. Chem. Soc. 93, 3184(1971)). A total of 3.6 mg of the compound was dissolved in 2.0 ml dimethyl sulfoxide (D-5879, Sigma Chemical St. Louis, Mo.) and the resultant solution was then added slowly, with stirring, to 1300 ml silicone rubber forming solution (Water Based Emulsion #3-5024, Dow Corning Midland, Mich.). A 35 microliter aliquot of the mixture was subsequently dispensed into each well of a 96 well, flat bottom, white microtiter tray (#011-010-7901, Dynatech Chantilly, Va.), and the system was subsequently cured overnight in a low humidity (less than 25% RH), 60° C. incubator. After curing, the trays were washed by either soaking or by filling and emptying each well several times with each of the following reagents; a) absolute ethanol, b) 0.1M phosphate buffer pH 7.2, c) hot distilled water (about 45° C.) and d) ambient temperature distilled water.

Subsequently, 150 microliters of a Broth A, consisting of 35% Mueller Hinton II (BBL #1243322, BD Microbiology Systems, Cockeysville, Md.), 15% Brucella (BBL #11088), and 50% distilled water, was dispensed into each well of the tray, and the tray was then placed in a glove box containing the desired concentration of oxygen, mixed with nitrogen to obtain a total pressure of 1 arm. The tray was kept in the glove box for at least 24 hours, after which it was covered with an adhesive backed mylar sheet and removed.

The fluorescent emissions of the fluorescent compound in the bottom of each well of the tray was then measured using a Perkin-Elmer LS-SB equipped with a microtiter reader attachment at the following instrument settings: 485 nm excitation wavelength, 550 nm cut-on filter in the emission window, 10 nm excitation slit, and a 5 nm emission slit. The results are presented in Table 1.

TABLE 1

Fluorescence of Tray Equilibrated with Various Oxygen Gas Levels

| Tray Mixture | Average Reading | % Oxygen in (balance Nitrogen) |
| --- | --- | --- |
| 1 | 803 | 0.00 |
| 2 | 759 | 0.28 |
| 3 | 738 | 0.53 |
| 4 | 524 | 2.45 |
| 5 | 484 | 3.40 |
| 6 | 445 | 5.35 |
| 7 | 208 | 20.9 |

As shown, it can be observed that indicators in wells in trays equilibrated in atmospheric air (Tray 7) displayed a much lower fluorescent signal than wells equilibrated with gas mixtures containing lower concentrations of oxygen (Trays 1–6). This indicates that the fluorescent emission of the fluorescent indicator compound embedded in the silicone rubber is related to oxygen concentration and that the system can be easily equilibrated with changing oxygen levels. The system allowed 96 sample wells (containing 0.1–0.3 ml sample) to be contained in a single unit that is easily manipulated.

EXAMPLE 2

Use of Indicator System to Measure Relative $O_2$ Concentration Produced by a Reducing Agent The $O_2$ concentration in wells of an Indicator Microtiter tray produced as in Example 1 was varied by the addition of a strong reducing agent, sodium sulfite (which reduces $O_2$ content). A 150 microliter aliquot of the reducing agent (at concentrations ranging from 0 to 1083 parts per million (ppm) sulfite ion in water) was pipetted into wells of the tray. Each well was allowed to react for 30 minutes, open to the atmosphere, and the fluorescence of the indicators measured in a Fluoroskan II Fluorometer (Flow Laboratories, McLean, Va.), having an excitation bandpass filter at a wavelength of 460 nm and an emission cut-on filter at 570 nm. The results are presented in Table 2.

TABLE 2

Effect of Sodium Sulfite on Fluorescence

| ppm sulfite ion | Fluorescence Intensity* |
| --- | --- |
| 0 | 3090 |
| 65 | 3513 |
| 163 | 3545 |
| 325 | 4033 |
| 542 | 11571 |
| 1083 | 11863 |

*Mean of 4 wells

As shown, the wells containing the highest concentrations of reducing agent (and, consequently, the lowest $O_2$ concentration) have the highest fluorescence intensity, thus demonstrating the relationship between $O_2$ concentration and fluorescence.

EXAMPLE 3

Use of Indicator System to Determine the Presence of a Microorganism

Figure 1:
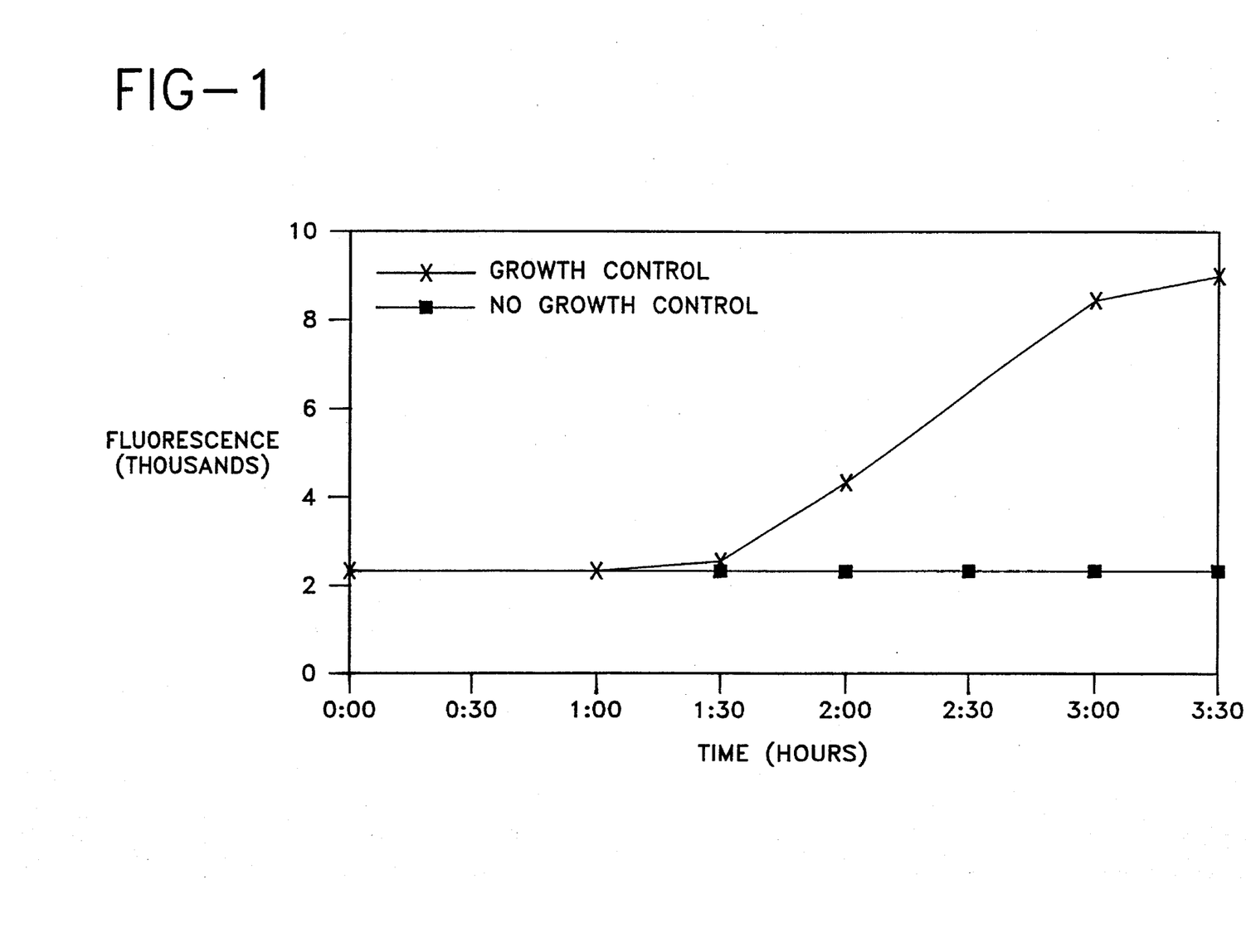
FIG. 1 graphically depicts intensity of fluorescence as a function of time for indicators in contact with broth containing organisms and broth containing no organisms.

A 0.5 McFarland suspension of *E. coli* (ATCC #25922), containing about $1.5 \times 10$ CFU/ml, was prepared using an A-Just nephelometer (Abbott Labs, Chicago, Ill.). The suspension was diluted to about $1 \times 10^7$ CFU/ml in Broth A (see Example 1). A 150 microliter aliquot of this suspension was placed into indicator tray wells prepared as in Example 1, and subsequently incubated at 37° C. At intervals, the fluorescence was measured in a Fluoroskan II fluorometer over the period of 1–3½ hours. An increased fluorescence signal was observed over time as shown in FIG. 1. The fluorescence signal from wells containing no organisms showed very little change. The wells containing organisms were significantly brighter when visually observed under a UV light source. Thus, it appears that the metabolic activity of the organisms in the wells caused the fluorescence signal to increase (presumably by decreasing the $O_2$ concentration).

EXAMPLE 4

Dependence of Fluorescence Change on Organism Concentration

Figure 2:
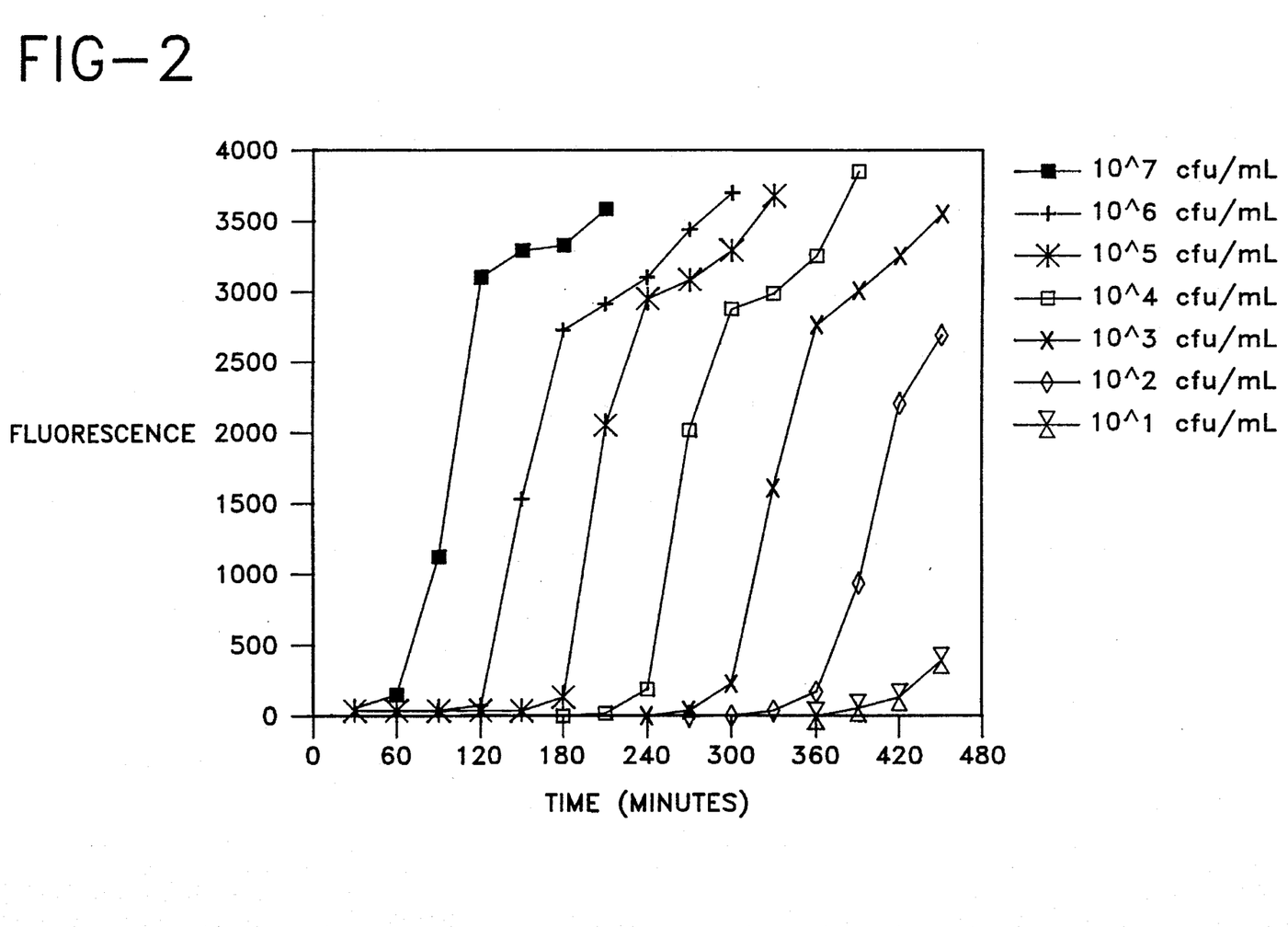
FIG. 2 graphically depicts the intensity of fluorescence as a function of time for indicators in contact with broth inoculated with different concentrations of microorganisms.

A 0.5 McFarland suspension of *E. coli* (ATCC #25922) in sterile trypticase soy broth (TSB, BBL #11768) was made using an A-Just nephelometer (Abbott Labs. Chicago, Ill.). A series of *E. coli* suspensions ranging from $1 \times 10^7$ CFU/ml to about 10 CFU/ml were made by making serial dilutions. A 200 microliter aliquot of each suspension was placed into 8 wells of an indicator tray prepared as in Example 1. The tray was then incubated at 37° C. and the fluorescence measured every 30 minutes in a Fluoroskan II fluorometer. The fluorescence of the 8 wells were averaged and corrected by subtracting the background fluorescence of a sterile TSB well. The change in fluorescence over time is shown in FIG. 2.

As shown, a change in the starting concentration of the organism by a factor of 10 (one log unit) caused a delay of about 1 hour for the fluorescence in the well to exceed 2000 fluorescence units. It is postulated that this delay is due in part to the fact that the system is open to the atmosphere. Oxygen in the air can and does freely diffuse into the medium in an attempt to replace that consumed by the microorganisms. It is further postulated that only when the organisms are present in or have multiplied to sufficient numbers and are metabolically active enough to consume oxygen at a rate approximating or faster than the rate at which oxygen diffuses into the test solution, will the fluorescent signal generated by the indicator element in the bottom of the reservoir show an increase.

EXAMPLE 5

Preparation of an Indicator Microtitration Tray with an Alternate Fluorescent Indicating Molecule A 96 well Microtiter tray was produced essentially as in Example 1, except that tris-(2,2'-bipyridyl)-ruthenium (II) chloride hexahydrate (Aldrich Chemical Company, Milwaukee, Wis.) [Ru(BiPy)$_3$Cl$_2$] was substituted for Ru(DPP)$_3$Cl$_2$ in the silicone mixture. A second tray containing 9,10-diphenyl anthracene (DPA) was also prepared. All wells were charged with 150 ul of $1 \times 10^7$ CFU/ml *E. coli* (ATCC #25922) in broth. Table 3 lists the results at 0, 1, 2, 3, and 4 hours after addition of organisms.

TABLE 3

Fluorescence Counts for Devices with Different Fluorophores

| Fluorescent Compound | Silicone | 0 hr. | 1 hr. | 2 hr. | 3 hr. | 4 hr. |
|---|---|---|---|---|---|---|
| $Ru(DPP)_3Cl_2$ (Ex. 3) | A | 2300 | 2315 | 2560 | 8329 | 9000 |
| $Ru(BiPy)_3Cl_2$ (Ex. 5) | A | 2866 | — | 3449 | 3951 | 4109 |
| DPA (Ex. 5) | A | 1300 | — | 1385 | 1456 | 1572 |
| $Ru(DPP)_3Cl_2$ (Ex. 6) | B | — | 995 | 4334 | 3775 | 3508 |

A = Dow-Corning 3-5024 water-based silicone
B = Wacker white SWS-960+ silicone

As shown, both fluorescent sensor compounds exhibited large increases with fluorescence over time, indicating their suitability for use in this system.

EXAMPLE 6

Preparation of an Indicator Microtitration Tray Using an Alternative Silicone

To demonstrate that the fluorophore can function when embedded in a different matrix, a 96 well Microtiter tray was produced essentially as in Example 1. In this experiment, 10 ul of white SWS-960 RTV silicone (Wacker Silicones, Adrian, Mich.) containing 10 milligrams of $Ru(DPP)_3Cl_2$ per liter was dispensed into each well of the tray and allowed to cure. No wash steps were performed on the resultant tray. The results are presented in Table 3. As in Example 1, wells containing 150 ul of $1 \times 10^7$ CFU/ml E. coli (ATCC #25922) in broth had a much greater fluorescent intensity after several hours at 37° Centigrade.

EXAMPLE 7

Effect of Toxic Substances on the Oxygen Consumption of Microorganisms

Figure 3:
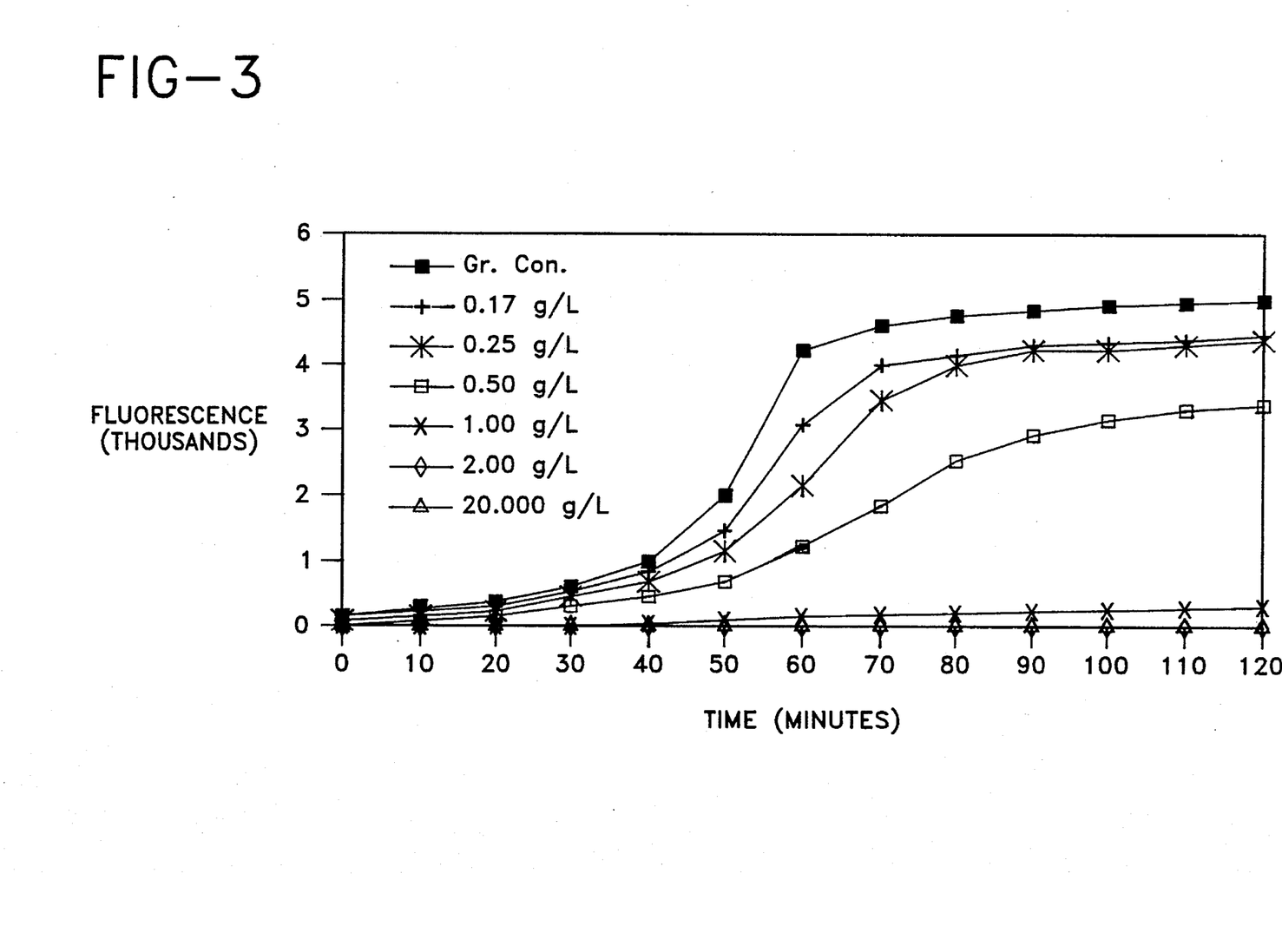
FIG. 3 graphically depicts the intensity of fluorescence as a function of time for indicators in contact with broth inoculated with the same number of organisms but containing different concentrations of phenol.
Figure 4:
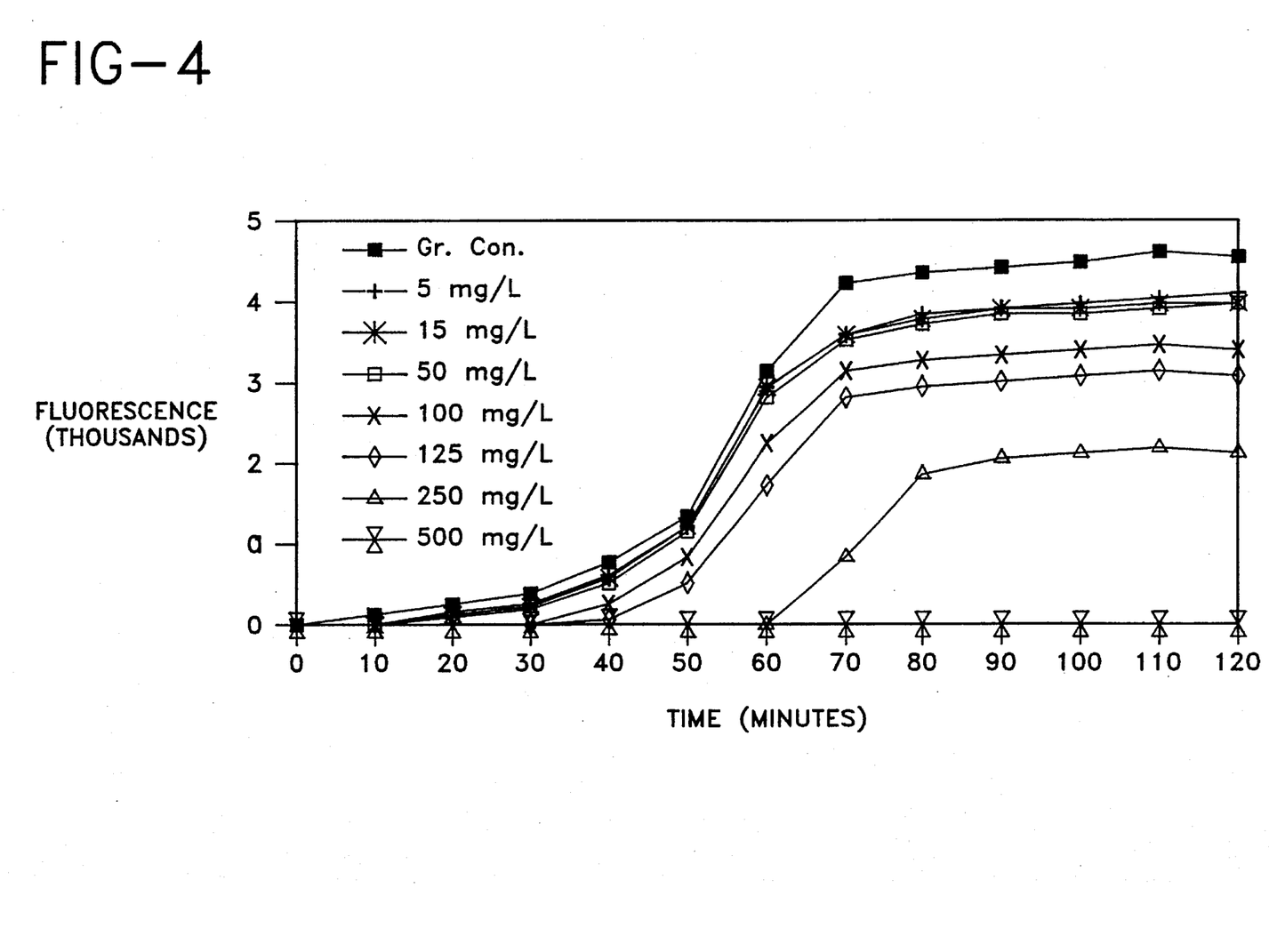
FIG. 4 graphically depicts the intensity of fluorescence as a function of time for indicators in contact with broth inoculated with the same number of organisms but containing different amounts of copper sultate.

A suspension containing about $3 \times 10^8$ CFU/ml, of *Pseudomonas aeruginosa* (ATCC #10145) in Broth A was prepared using an A-Just nephelometer. A total of 150 ul of the suspension was placed in each well of the indicator trays prepared as in Example 1; these suspensions were then diluted with solutions of phenol or copper sulfate (which are deleterious to microbial growth) to a final concentration of $1.5 \times 10^8$ CFU/ml. The trays were incubated at 37° C. and their fluorescence measured in a Fluoroskan II at 10 minute intervals. FIGS. 3 and 4 show the effect of phenol and copper sulfate on the response of the system.

As shown, at high levels of additives, growth was suppressed and the fluorescence did not increase with time. Wells containing phenol at 1 gram/liter or more, and copper sulfate at greater than 500 mg/liter, had no increase in fluorescence signal at times less than two hours, indicating absence of actively metabolizing organisms. Thus, measurement of oxygen consumption can be used to probe the metabolism of the organisms.

EXAMPLE 8

Effect of Antibiotics on E. coli

A 0.5 McFarland suspension of *E. coli* (ATCC #25922) in Broth A (see Example 1) was prepared using an A-Just nephelometer. The suspension was diluted to $1 \times 10^7$ CFU/ml in wells of an indicator tray prepared as in Example 1 containing the antibiotics ciprofloxacin, cefoxitin and cefuroxime at final concentrations of 0.5 to 8 ug/ml. The trays were incubated at 37° C. for 4 hours and their fluorescence measured in a Fluoroskan II fluorometer. The results are presented in Table 4.

TABLE 4

Fluorescence from an Indicator Tray Containing
E. coli and Antibiotics
Relative Fluorescence at 4 hrs.

| Antibiotic Concentration (ug/mL) | Ciprofloxacin | Cefuroxime | Cefoxitin |
|---|---|---|---|
| 0.5 | 2537 | 7902 | 8181 |
| 1 | 2621 | 7983 | 8270 |
| 2 | 2461 | 7161 | 7120 |
| 4 | 2527 | 7598 | 3692 |
| 8 | 2424 | 6469 | 2974 |

As shown at all concentrations, the *E. coli* was sensitive to ciprofloxacin and low fluorescence counts were observed. The *E. coli* was resistant to the concentrations of cefuroxime and high fluorescence counts were observed. The *E. coli* was resistant to the 0.5, 1, and 2 ug/ml concentrations of cefoxitin and high counts were observed, but it was sensitive to the higher concentrations of cefoxitin and low counts were observed for 4 and 8 ug/ml. Thus, there is a correlation between the fluorescence and antibiotic concentration, demonstrating that the system of this invention can be used to assess the effects of antimicrobics and to determine the minimum effective concentration compositions.

EXAMPLE 9

Effect of Antibiotics on the Oxygen Consumption of *E. coli* with $Ru(BiPy)_3Cl_2$ Fluorescence Indicator A 0.5 McFarland suspension of *E. coli* (ATCC #25922) in Broth A (see Example 1) was prepared using an A-Just nephelometer. The suspension was diluted to $1 \times 10^7$ CFU/ml in Wells of an indicator tray prepared as in Example 5 ($Ru(BiPy)_3Cl_2$ indicator) containing the antibiotics ciprofloxacin, cefoxitin and cefuroxime at final concentrations of 0.5 to 8 ug/ml. The trays were incubated at 37° C. for 4 hours and their fluorescence measured in a Fluoroskan II fluorometer. The results are listed in Table 5.

TABLE 5

Fluorescence from an Indicator Tray Containing
E. coli and Antibiotics
Relative Fluorescence at 4 hrs.

| Antibiotic Concentration (ug/mL) | Ciprofloxacin | Cefuroxime | Cefoxitin |
|---|---|---|---|
| 0.5 | 507 | 1155 | 1171 |
| 1 | 428 | 1539 | 1491 |
| 2 | 308 | 1183 | 1338 |
| 4 | 403 | 1170 | 832 |
| 8 | 323 | 1194 | 559 |

As shown, as in Example 8, at these concentrations the *E. coli* is sensitive to ciprofloxacin and low fluorescence counts were observed. The *E. coli* is resistant to these concentrations of cefuroxime and high fluorescence counts were observed. The *E. coli* is resistant to the 0.5, 1, and 2 ug/ml concentrations of cefoxitin, high counts were observed; it was sensitive to higher concentrations of cefoxitin and lower counts were observed for 4 and 8 ug/ml. Thus, the results indicated that Ru(BiPy)$_3$Cl$_2$ can also be used in a fluorescence indicator.

EXAMPLE 10

Effect of Antibiotics on the Oxygen Consumption of Microorganisms Using DPA Fluorescence Indicator A 0.5 McFarland suspension of *E. coli* (ATCC #25922) in Broth A was prepared using an A-Just nephelometer. The suspension was diluted to 1×10$^7$ CFU/ml in wells of an indicator tray prepared as in Example 5 (DPA indicator) containing the antibiotics ciprofloxacin, cefoxitin and cefuroxime at final concentrations of 0.5 to 8 ug/ml. The trays were incubated at 37° C. for 4 hours and their fluorescence measured in a Fluoroskan II. The results are presented in Table 6.

TABLE 6

Fluorescence from an Indicator Tray Containing *E. coli* and Antibiotics
Relative Fluorescence at 4 hrs.

| Antibiotic Concentration (ug/mL) | Ciprofloxacin | Cefuroxime | Cefoxitin |
|---|---|---|---|
| 0.5 | 91 | 183 | 192 |
| 1 | 109 | 197 | 173 |
| 2 | 94 | 195 | 164 |
| 4 | 74 | 160 | 101 |
| 8 | 68 | 161 | 95 |

As shown, at these concentrations the *E. coli* is sensitive to ciprofloxacin and low fluorescence counts were observed. The *E. coli* is resistant to these concentrations of cefuroxime and high fluorescence counts were observed. The *E. coli* is resistant to the 0.5, 1, 2 ug/ml concentration of cefoxitin, high counts were observed; it was sensitive to higher concentrations and lower counts were observed for 4 and 8 ug/ml as in Examples 8 and 9, indicating that DPA is also useful as a fluorescence indicator.

EXAMPLE 11

Effect of Open and Closed Systems on Oxygen Measurements

Figure 5A:
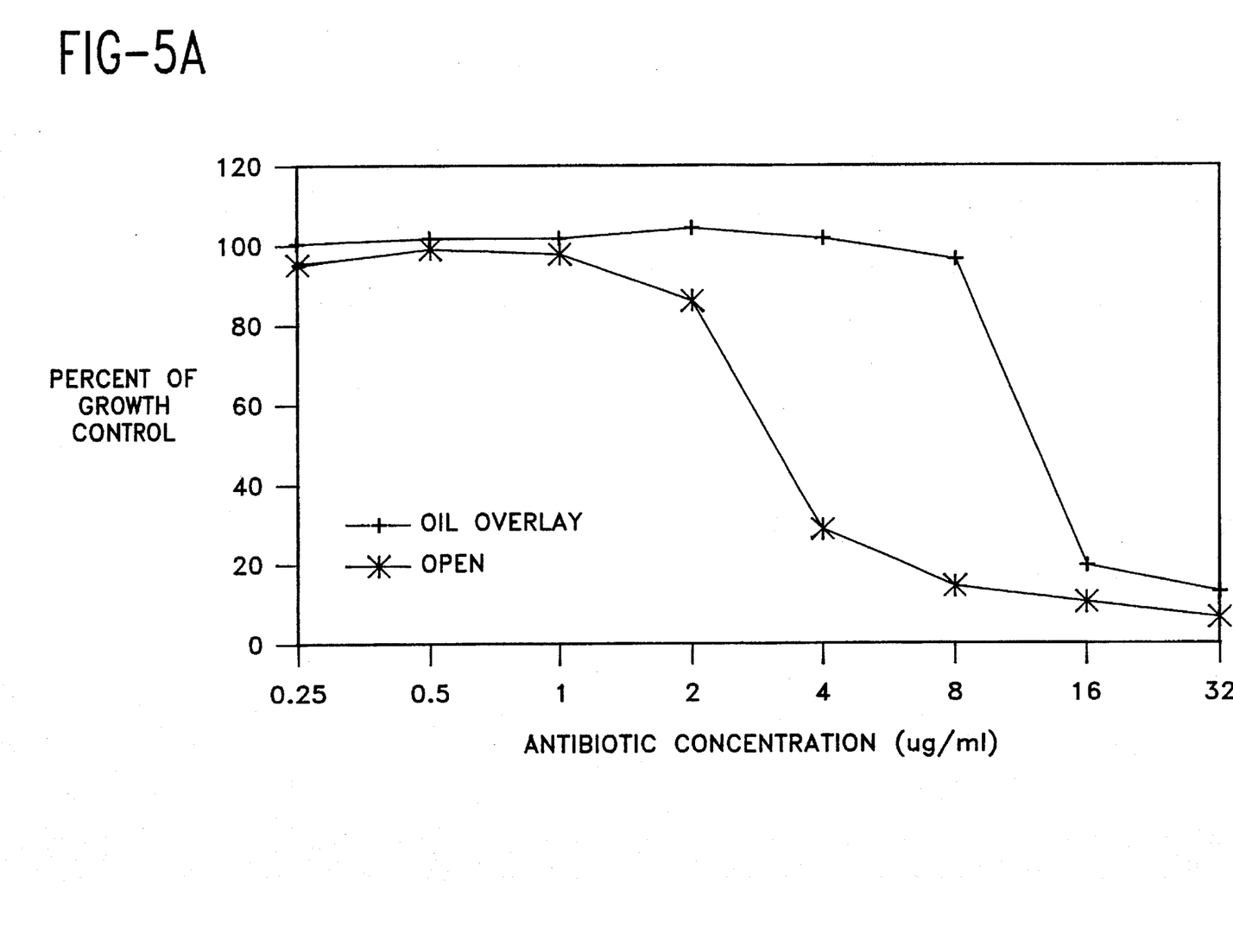
FIG. 5A graphically depicts the fluorescence, as a function of indicators in contact with broth inoculated with the same concentration of microorganisms but different concentrations of cefuroxime. Some wells were covered with mineral oil to prevent oxygen from diffusing into the wells. The fluorescence is given as a percent of growth control.
Figure 5B:
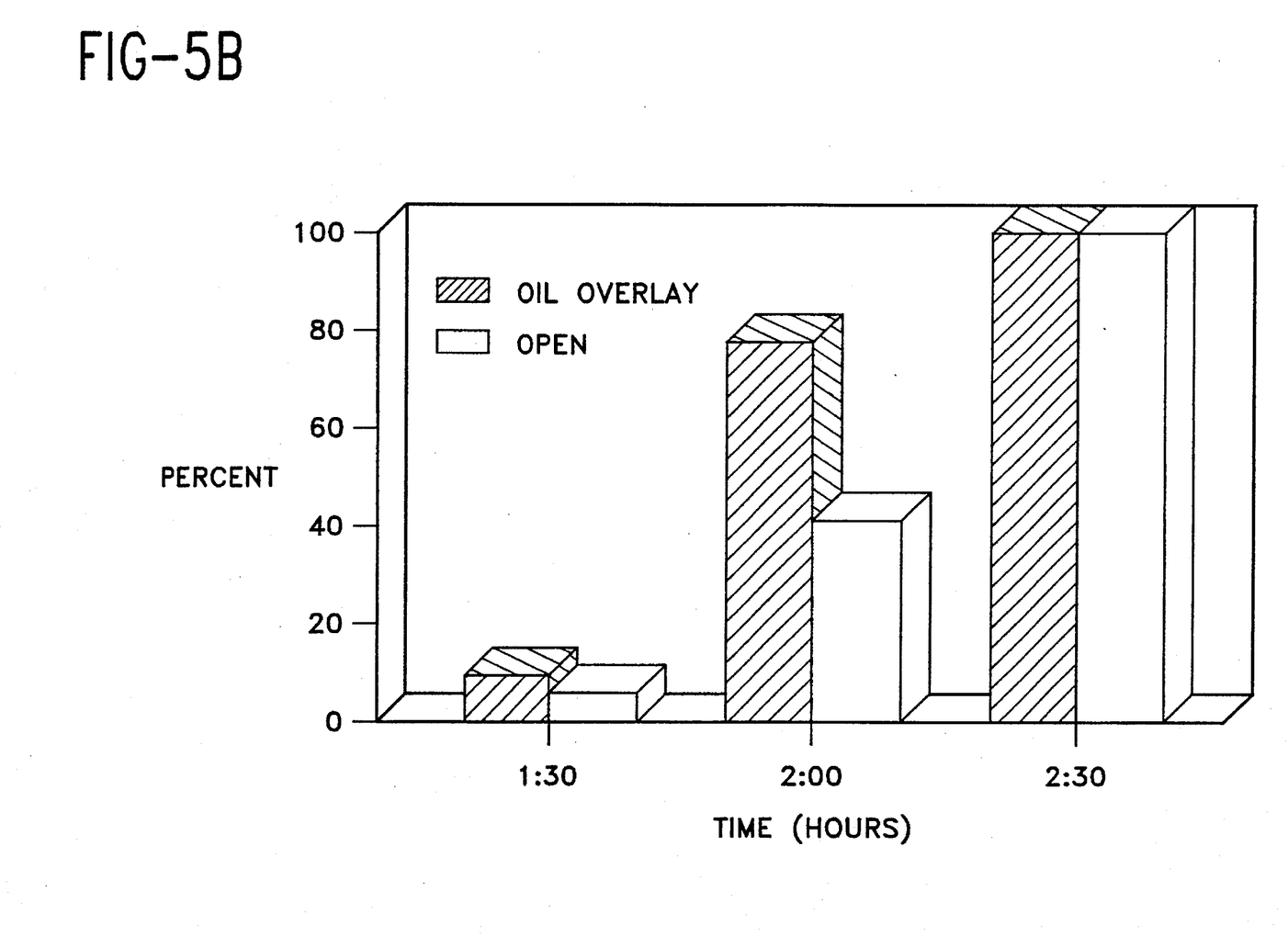
FIG. 5B graphically depicts the fluorescence as a percent of the growth control in wells that are overlaid with oil or left open and measured at several different times.

A 96 well indicator microtiter tray was produced substantially as in Example 1. Duplicate wells in the tray were supplemented with the antibiotic cefuroxime in the concentration range of 0.25 to 32 ug/ml. One hundred and fifty microliters of a suspension of *E. coli* (ATCC #11775) was added to the wells to yield about 3×10$^7$ CFU/ml. One of each duplicate well was overlaid with mineral oil to inhibit diffusion of oxygen into the wells, the other duplicate was left open to the air. The tray was incubated at 37° C. for 5 hours, the fluorescence was measured in a Fluoroskan II fluorometer and that fluorescence was compared with the average of several wells containing no antibiotic to yield a percent of the growth control at each antibiotic concentration. FIG. 5A shows the behavior of the open and covered wells at five hours as a function of cefuroxime concentration. FIG. 5B shows the change in fluorescence of the growth control wells when open or overlaid with mineral oil.

The "closed system" overlaid with mineral oil did not show an effect on oxygen consumption by the 4 and 8 ug/ml concentrations of antibiotic while those wells with no mineral oil showed correctly that this organism is sensitive to cefuroxime at these concentrations. This difference is due, presumably to the time lag needed for the antibiotic to affects the organism; it is believed that during this time the oxygen is brought to an artificially low level by the ongoing metabolic activity of the organisms.

Thus, to utilize the invention with optimum sensitivity for the detection of the effect of toxins on organisms, the sample reservoir is beneficially open to the influx of oxygen.

EXAMPLE 12

The Effect of Sample Volume on Indicator Trays

A 0.5 McFarland suspension of *E. coli* (BDMS Culture collection #7133) was diluted to 1×10$^7$ CFU/ml in Broth A. Different volumes (from 10 ul to 300 ul) of the diluted suspension were placed into wells of an indicator tray produced as in Example 1. The tray was incubated at 37° C. and the fluorescence measured in a Fluoroskan II at 30 minute intervals. Fluorescence from the same volume of sterile broth was subtracted to give the fluorescence change cause by the microorganism. The results are presented in Table 7.

TABLE 7

Effect of Sample Volume on Indicator Tray Fluorescence
Relative Fluorescence

| Sample Volume (ul) | 0 hr. | 1 hr. | 2 hr. | 2.5 hr. | 3 hr. | 3.5 hr. | 4 hr. |
|---|---|---|---|---|---|---|---|
| 10 | 0 | 0 | 0 | 0 | 0 | 4 | 139 |
| 20 | 0 | 0 | 275 | 795 | 814 | 1218 | 1958 |
| 40 | 0 | 245 | 683 | 1883 | 2108 | 2613 | 3240 |
| 60 | 0 | 80 | 1559 | 3497 | 4847 | 6226 | 6827 |
| 80 | 0 | 82 | 1798 | 5340 | 8333 | 8810 | 8801 |
| 100 | 0 | 31 | 1848 | 5952 | 7672 | 7962 | 7961 |
| 125 | 0 | 103 | 2798 | 6286 | 7580 | 7852 | 7852 |
| 150 | 0 | 32 | 2539 | 6005 | 6568 | 6759 | 6686 |
| 175 | 0 | 51 | 2574 | 6149 | 6993 | 6987 | 6798 |
| 200 | 0 | 59 | 2376 | 5355 | 5742 | 5944 | 5826 |
| 250 | 0 | 115 | 2172 | 5373 | 5695 | 5822 | 5759 |
| 300 | 0 | 107 | 2538 | 4650 | 4727 | 4825 | 4778 |

Briefly, it was observed that those wells with 40 ul or less of sample showed less than ½ the increase in relative signal observed in wells with 80 ul or more at times of 2 hours or more. It is believed that in the wells containing 40 ul or less, too little volume was present for the organisms to effectively consume oxygen faster than it could diffuse into the small volumes of sample.

EXAMPLE 13

Use of Indicator System Without a Fluorometer

Indicator trays were prepared using the same fluorescent compound and silicone as in Example 1. However, the trays were made of clear plastic and the wells had round bottoms (#4-3918-2, BD Labware Lincoln Park, N.J.). Two nanograms of Ru(DPP)$_3$Cl$_2$ in 10 ul of silicone were placed in each well of the tray and no wash steps were performed. Samples of *Ps. aeruginosa* (BDMS Culture collection #N111) and *E. coli* (ATCC #25922) were diluted to Broth A (see Example 1) 1×#10$^7$ CFU/ml in Broth A containing either 0 to 32 ug/ml cefuroxime, 0.12 to 8 ug/ml ciprofloxacin or 0 to 32 ug/ml cefoxitin and charged to the trays. The trays were incubated for 4 hours at 37° C. and subsequently placed on the stage of an ultraviolet transilluminator (#TX-365A, Spectronics Corp., Westbury, N.Y.) which served as an excitation source. The resulting fluorescence was observed from directly above the trays at a distance of 1 foot through a 550 cut-on filter (#LL-550-S-K962, Corion, Holliston, Mass.). It was readily observed that wells which contained either no antibiotics or concentrations of antibiotics that did not affect the organisms demonstrated a high level of fluorescence. Wells with either no organisms or higher antibiotic levels had a much lower level of fluorescence. The lowest concentration of antibiotic to significantly lower the fluorescent emissions for each organism is shown in Table 8 along with the MIC concentration determined using an overnight microdilution antimicrobial susceptibility test.

TABLE 8

Fluorescence Results Obtained Without Use of an Instrument MIC

|  | Cefuroxime | | Ciprofloxacin | | Cefoxitin | |
|---|---|---|---|---|---|---|
|  | Visual | Reference | Visual | Reference | Visual | Reference |
| Ps. aeruginosa | >64 | >64 | 1 | 0.5 | >64 | >64 |
| E. coli #25922 | 16 | 8 | <0.12 | <0.12 | 8 | 4 |

EXAMPLE 14

Use of Indicator to Detect the Presence of a Low Level of Bacteria In a Medium Containing Blood Tissue culture flasks (Falcon #3084, BD Labware, Lincoln Park, N.J.) were prepared with one side coated with 3 mls of Dow Corning Water-based Emulsion containing 68 ng of Ru(DPP)$_3$Cl$_2$. The flasks were sterilized using ethylene oxide. One hundred thirty five mls of TSB broth (BBL #11768) containing about 0.05 CFU/ml E. coli (ATCC #25922) and 15 mls of defibrinated sheep blood was added to one of the flasks. A control flask contained 135 mls of TSB and 15 mls of blood but no organisms. The caps of the flasks were loosened to allow air circulation and the flasks were incubated at 37° C. in an upright position. A fiber optic probe allowed the fluorescence from the flasks to be measured by a Perkin Elmer LS-5B spectrofluorometer located several feet from the incubator. The fluorometer measured the flasks at 485 nm excitation wavelength with a 10 nm slit width and a 550 nm cut-on emission filter. A strip chart was attached to the fluorometer and the fluorescence monitored continuously for 16 hours. At 7.5, 10.5 and 16 hours during the incubation period a 100 ul aliquot was removed from the test flask, diluted 1:100 in sterile TSB and 100 ul of the dilution was spread on each of three TSA plates to determine the number of CFU/ml present in the flask. The results are graphically depicted in FIG. 6.

Figure 6:
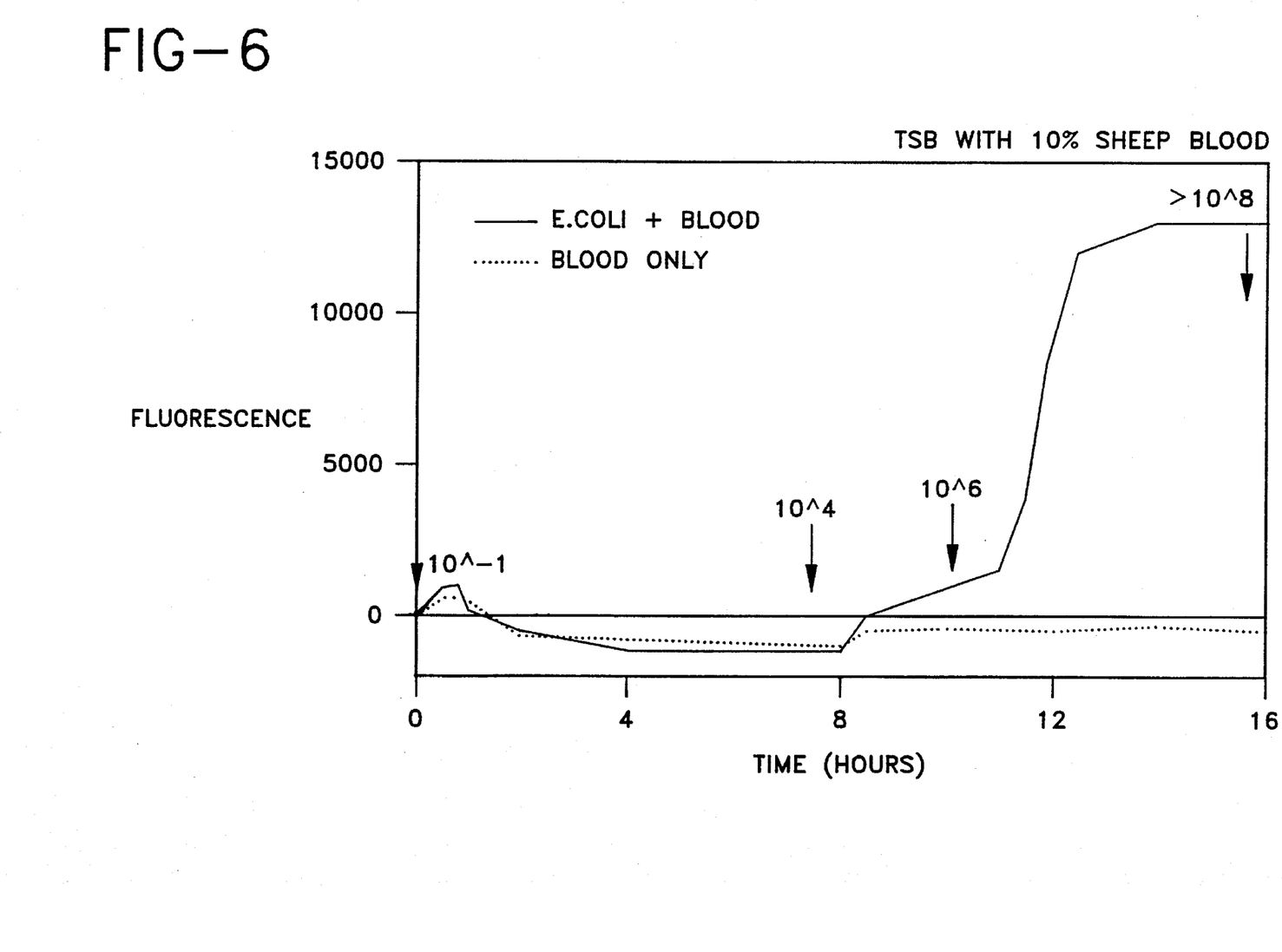
FIG. 6 graphically depicts the intensity of fluorescence of indicators in blood culture bottles when measured continuously over 16 hours. The arrows indicate the times when samples were removed in order to quantify the concentration of organisms present.

As shown, the non-invasive techniques of this invention can be used for the detection of organisms in blood, a very critical and demanding task. The flask contained a very cloudy and turbid solution which is continuously monitored for sixteen hours, and measurement of fluorescence showed a direct correlation to the growth of organisms. This growth was readily detected by 11 hours, when the concentration of organisms had just exceeded 10$^6$ CFU/ml.

EXAMPLE 15

Indicator Coated on the Spherical Ends of FAST Tray Lid Prongs

This example monitored bacterial respiration with oxygen indicators coated on the spherical ends of FAST™ tray (Becton Dickinson) lid prongs. Three different indicators were evaluated.

The first indicator prepared was a mixture of 1 ml of 2 mg/ml dichloromethane solution of Ru(DPP)$_3$Cl$_2$ and 10 ml Dow-Corning 3-5024 water-based silicone emulsion. The spherical ends of FAST tray lid prongs were dipped into a shallow reservoir of the indicator solution, removed, placed prong side down in a rack, and allowed to cure by evaporation. The second indicator was prepared by mixing 3 mL Wacker SWS-960 clear silicone dispersion, 6 mL petroleum ether, and 0.5 mL of the 2 mg/mL dichloromethane solution of Ru(DPP)$_3$Cl$_2$. The spherical ends of FAST tray lid prongs were coated with this indicator in the same manner as with the first indicator and allowed to cure by evaporation of the solvents and reaction with atmospheric moisture. The third indicator was prepared in the same manner as the second but Wacker SWS-960 white silicone was used.

A 1×10$^7$ CFU/mL suspension of E. coli ATCC #25922 in Mueller Hinton broth was prepared; 150 microliter aliquots were pipetted into the odd numbered rows of a microtiter tray, while 150 microliter aliquots of uninoculated Mueller Hinton broth were pipetted into the wells of the even numbered columns. The lids containing the indicator coated prongs were placed on the trays. The lidded trays were placed in a 37° C. high humidity incubator for 3 hours.

Following the three hour incubation, the trays were placed on a transparent glass plate. A mirror was positioned below the glass plate in such a manner that the bottom of the tray was visible in the mirror. A 365 nm ultraviolet source which evenly illuminated the entire tray was positioned about one inch from the top of the tray. A box, with a small window through which the mirror could be seen, was placed over the assembly to block room light, and a 550 nm cut-on filter was placed in the box window. With this assembly the fluorescence from the indicator coated spherical ends of the FAST tray lid prongs could be visualized through the tray bottom. Table 9 contains the results of visual observations of the trays evaluated in this manner.

TABLE 9

Visual Observations of Indicator Coated Lid Prongs Viewed Through Tray Bottoms

| Silicon | Observations |
|---|---|
| Dow-Corning | Very bright fluorescence from spheres immersed in organism containing wells. Very weak fluorescence from prongs in uninoculated wells. |
| Wacker Clear | Some visible difference between prongs immersed in inoculated and uninoculated wells. Difference much less observable than with Dow-Corning indicator. |
| Wacker White | Very bright fluorescence from |

TABLE 9-continued

Visual Observations of Indicator Coated Lid Prongs Viewed Through Tray Bottoms

| Silicon | Observations |
|---|---|
|  | spheres immersed in inoculated wells, intensity about equal to Dow-Corning indicator. Some weak fluorescence from spheres in uninoculated wells. |

Thus, all three indicator systems produced desirable results, with the Dow Corning and Wacker White exhibiting much more distinguishable differences between the inoculated and uninoculated wells.

EXAMPLE 16

Indicators Consisting of Ru(DPP)$_3$Cl$_2$ Adsorbed on Silica Gel Particles Embedded in UV Cured Silicone Rubber Indicators were prepared by adsorbing Ru(DPP)$_3$Cl$_2$ onto silica gel particles and embedding these particles into Loctite Nuva-Sil silicone rubbers. A variety of indicators were prepared using silica gel particles of different mesh sizes, different amounts of adsorbed fluorophore, different ratios of silica gel to silicone, and two types of Loctite Nuva-Sil (Nuva-Sil 5091 and Nuva-Sil 5147). Table 10 contains the characteristics of the indicators prepared and the visual results obtained from the indicators in contact with microorganism suspensions. An exemplary procedure used for the preparation of the indicators is presented below.

Ten grams of 100–200 mesh Davisil silica gel (Aldrich, Milwaukee, Wis.) was weighed into a 500 mL round bottom evaporation flask. Forty three milliliters of a 0.14 mg/mL ethanol solution of Ru(DPP)$_3$Cl$_2$ was pipetted into the flask. The ethanol was removed by rotary vacuum evaporation resulting in the adsorption of the Ru(DPP)$_3$Cl$_2$ on the silica gel at a concentration of 0.6 mg Ru(DPP)$_3$Cl$_2$/gm silica gel. Four grams of this silica gel were mixed with 16 g Loctite Nuva-Sil 5091 (Loctite, Newington, Conn.) resulting in a 20% w/w silica/silicone ratio. Twenty-five microliter aliquots of this mixture were pipetted into the wells of a microtiter tray. The silicone was cured by exposure to high intensity ultraviolet radiation for 15 seconds in a Loctite Zeta 7200 UV curing chamber. The other indicators in Table 10 were similarly prepared.

To evaluate the indicators, 150 microliters of a 1×10$^7$ CFU/mL suspension of E. coli (ATCC #25922 in Mueller Hinton II broth (BBL) was pipetted into selected wells of the microtiter tray; uninoculated broth was pipetted into other wells. The tray was incubated in a high humidity 35° C. incubator for 3 hours. To visualize the fluorescence from the indicator the tray was placed on the stage of a 365 nm UV transilluminator; the fluorescence from the indicator was observed from above through a 550 nm cut-on filter. A "+" sign in the Response column of Table 10 indicates that a visibly discernable increased fluorescence was observed from the wells containing the organism.

TABLE 10

Indicator Formulations and Responses

| Mesh Size | mg Ru(DPP)$_3$Cl$_2$/g Silica | Wt % Silica | Silicone | Response |
|---|---|---|---|---|
| 60–100 | 0.2, 0.4, 0.6 | 5, 10, 20 | 5091, 5147 | +* |
| 100–200 | 0.2, 0.4, 0.6 | 5, 10, 20 | 5091, 5147 | +* |
| 200–425 | 0.2, 0.4, 0.6 | 5, 10, 20 | 5091, 5147 | +* |

*Represents result from all 18 trials (9 each for Silicone 5091 and 5147).

In replicate trials utilizing wells with no microorganisms, the indicators displayed little or no light (although at higher (0.6 mg/gm) concentrations of indicator, a dim fluorescence was noted).

It is apparent that many modifications and variations of this invention as hereinabove set forth may be made without departing from the spirit and scope hereof. The specific embodiments described are given by way of example only and the invention is limited only by the terms of the appended claims.

What is claimed is:

1. A method for detecting the presence of respiring microorganisms in a fluid comprising:
   (i) contacting said fluid with a sensor composition which comprises a fluorescent compound that exhibits a reduction in fluorescent intensity, when irradiated with light containing wavelengths which cause said compound to fluoresce, upon exposure to oxygen, wherein the presence of the sensor composition is non-destructive to the microorganism;
   (ii) irradiating said sensor composition with light containing wavelengths which cause said fluorescent compound to fluoresce;
   (iii) measuring or visually observing the fluorescent light intensity from said fluorescent compound while irradiating said sensor compound with said light;
   (iv) comparing said measurement to that of a control not containing a respiring microorganism, wherein said control is selected from the group consisting of: a reagent control not in contact with respiring microorganisms and a calculated threshold, wherein a change in fluorescent intensity relative to the fluorescent intensity of the control is indicative of the presence of respiring microorganisms; and
   (v) in the event that no such increase is measured or observed, repeat steps (ii), (iii), and (iv) as needed, to detect the presence of respiring microorganisms in said fluid.

2. The method of claim 1 where said matrix is a rubber or plastic matrix.

3. The method of claim 1 wherein said matrix is a silicone rubber matrix.

4. The method of claim 1 wherein said fluorescent compound is adsorbed on solid silica particles.

5. The method of claim 1 wherein said fluorescent compound is a tris-4,7-diphenyl-1,10-phenanthroline ruthenium (II) salt.

6. The method of claim 5 wherein said fluorescent compound is tris-4,7-diphenyl-1,10-phenanthroline ruthenium (II) chloride.

7. The method of claim 1 wherein said fluorescent compound is a tris-2, 2'-bipyridyl ruthenium (II) salt.

8. The method of claim 7 wherein said fluorescent compound is tris-2,2'-bipyridyl ruthenium (II) chloride hexahydrate.

9. The method of claim 1 wherein said fluorescent compound is 9, 10-diphenyl anthracene.

10. The method of claim 1 wherein said fluid is isolated from atmospheric oxygen wherein said fluid is contained in a closed system.

11. The method of claim 1 wherein said fluid is exposed to atmospheric oxygen.

12. A method for determining the effects of an antibiotic or antimicrobial composition on a respiring microorganism comprising:

(i) preparing a broth of said microorganism:

(ii) contacting said broth with a sensor composition which comprises a fluorescent compound that exhibits a reduction in fluorescent intensity, when irradiated with light containing wavelengths which cause said compound to fluoresce, upon exposure to oxygen, wherein the presence of the sensor composition is non-destructive to the microorganism;

(iii) admixing with said broth, a quantity of said antibiotic or antimicrobial composition;

(iv) irradiating said sensor composition with light containing wavelengths which cause said fluorescent compound to fluoresce;

(v) measuring or visually observing the fluorescent light intensity from said fluorescent compound while irradiating said sensor compound with said light; and (vi) comparing said measurement to that of a control wherein said control is selected from the group consisting of: a reagent control not in contact with a respiring microorganism or the antibiotic or antimicrobial composition, a reagent control in contact with a respiring microorganism but not in contact with the antibiotic or antimicrobial composition and a calculated threshold, wherein a change in fluorescent intensity relative to the control is indicative of the susceptibility or resistivity of the microorganisms to the quantity of said antibiotic or antimicrobial composition; and (vii) in the event that no such change is measured or observed, repeat steps (iv), (v) and (vi), as needed, to determine the effects of the antibiotic or antimicrobial on the respiring microorganisms.

13. The method of claim 12 where said matrix is a rubber or plastic matrix.

14. The method of claim 12 wherein said rubber or plastic matrix is a silicone rubber matrix.

15. The method of claim 12 wherein said fluorescent compound is adsorbed on solid silica particles.

16. The method of claim 12 wherein said fluorescent compound is a tris-4,7-diphenyl-1,10-phenanthroline ruthenium (II) salt.

17. The method of claim 16 wherein said fluorescent compound is tris-4,7-diphenyl-1,10-phenanthroline ruthenium (II) chloride.

18. The method of claim 12 wherein said fluorescent compound is a tris-2, 2'-bipyridyl ruthenium (II) salt.

19. The method of claim 18 wherein said fluorescent compound is tris-2,2'-bipyridyl ruthenium (II) chloride hexahydrate.

20. The method of claim 12 wherein said fluorescent compound is 9, 10-diphenyl anthracene.

21. The method of claim 12 wherein said broth is isolated from atmospheric oxygen.

22. The method of claim 12 wherein said broth is exposed to atmospheric oxygen.

23. (amended) A method for detecting the presence of respiring microorganisms in a fluid comprising:

(i) contacting said fluid with a fluorescent sensor composition which comprises a fluorescent compound selected from the group consisting of tris-4,7-diphenyl-1,10-phenanthroline-ruthenium (II) chloride and tris-2, 2'-bipyridyl ruthenium (II) chloride hexahydrate, wherein the presence of the sensor composition is non-destructive to the microorganism;

(ii) irradiating said sensor composition with light containing wavelengths which cause said fluorescent compound to fluoresce;

(iii) measuring or visually observing the fluorescent light intensity from said fluorescent compound while irradiating said sensor compound with said light;

(iv) comparing said measurement to that of a control, wherein said control is selected from the group consisting of: a reagent control not in contact with respiring microorganisms and a calculated threshold, wherein a change in fluorescent intensity relative to the fluorescent intensity of the control is indicative of the presence of respiring microorganisms; and (v) in the event that no such increase is measured or observed, repeat steps (ii), (iii), and (iv), as needed, to detect the presence of respiring microorganisms in said fluid.

24. The method of claim 23 where said matrix is a rubber or plastic matrix.

25. The method of claim 23 wherein said matrix is a silicone rubber matrix.

26. The method of claim 23 wherein said fluorescent compound is adsorbed on solid silica particles.

27. The method of claim 23 wherein said fluid compound is isolated from atmospheric oxygen.

28. The method of claim 23 wherein said fluid compound is exposed to atmospheric oxygen.

29. A method of determining the effect of an antibiotic or antimicrobial composition on a respiring microorganism comprising:

(i) preparing a broth of said microorganism:

(ii) contacting said broth with a sensor composition which comprises a fluorescent compound selected from the group consisting of tris-4,7-diphenyl-1,10-phenanthroline-ruthenium (II) chloride and tris-2,2'-bipyridyl ruthenium (II) chloride hexahydrate, wherein the presence of the sensor composition is non-destructive to the microorganism;

(iii) admixing with said broth a quantity of said antibiotic or antimicrobial composition:

(iv) irradiating said sensor composition with light containing wavelengths which cause said fluorescent compound to fluoresce;

(iv) measuring or visually observing the fluorescent light intensity from said fluorescent compound while irradiating said sensor compound with said light;

(v) comparing said measurement to that of a control, wherein said control is selected from the group consisting of: a reagent control not in contact with a respiring microorganism or the antibiotic or antimicrobial composition, a reagent control in contact with a respiring microorganism but not in contact with the antibiotic or antimicrobial composition and a calculated threshold, wherein a change in fluorescent intensity relative to the control is indicative of the susceptibility or resistivity of the microorganisms to quantity of the antibiotic or antimicrobial composition: and (vi) in the event that no such change is measured or observed, repeat steps (iii), (iv), and (v), as needed, to detect the presence of respiring microorganisms in said fluid.

30. The method of claim 29 where said matrix is a rubber or plastic matrix.

31. The method of claim 29 wherein said matrix is a silicone rubber matrix.

32. The method of claim 29 wherein said fluorescent compound is adsorbed on solid silica particles.

33. The method of claim 29 wherein said broth compound is isolated from atmospheric oxygen wherein said fluid is contained in a closed system.

34. The method of claim 23 wherein said fluid compound is exposed to atmospheric oxygen.

* * * * *

UNITED STATES PATENT AND TRADEMARK OFFICE
CERTIFICATE OF CORRECTION

PATENT NO. : 5,567,598
DATED : October 22, 1996
INVENTOR(S) : David T. Stitt, Gregory J. Burrell, Kwok-Yu Hu, James F. Monthony, Robert Sapitowicz It is certified that error appears in the above-identified patent and that said Letters Patent is hereby corrected as shown below:

At Column 16, Line 43, in Claim 1, after "comprises a fluorescent compound", insert --, contained within a matrix which is relatively impermeable to water and non-gaseous solutes, but which has a high permeability to oxygen,--.

At Column 17, Line 29, in Claim 12, after "comprises a fluorescent compound", insert --, contained within a matrix which is impervious to water and non-gaseous solutes, but which has a high permeability to oxygen,--.

At Column 18, Line 21, in Claim 23, after "2'-bipyridyl ruthenium (II) chloride hexahydrate," insert --contained within a matrix which is relatively impermeable to water and non-gaseous solutes, but which has a high permeability to oxygen--.

At Column 18, Line 60, in Claim 29, after "ruthenium (II) chloride hexahydrate," insert --contained within a matrix which is relatively impermeable to water and non-gaseous solutes, but which has a high permeability to oxygen--.

Signed and Sealed this

Twenty-first Day of March, 2000

Attest:

Attesting Officer

Q. TODD DICKINSON

Commissioner of Patents and Trademarks